United States Patent [19]

Koch et al.

[11] Patent Number: 5,075,294
[45] Date of Patent: Dec. 24, 1991

[54] PYRIDYL PHOSPHATES, COMPOSITIONS CONTAINING THEM AND THEIR USE AS PESTICIDES

[75] Inventors: Volker Koch, Kelkheim; Günter Kratt, Eppstein; Stefan Schnatterer; Anna Waltersdorfer, both of Frankfurt am Main; Werner Knauf, Eppstein; Manfred Kern, Lörzweiler, all of Fed. Rep. of Germany

[73] Assignee: Hoechst Aktiengesellschaft, Frankfurt am Main, Fed. Rep. of Germany

[21] Appl. No.: 256,780

[22] Filed: Oct. 12, 1988

[30] Foreign Application Priority Data

Oct. 14, 1987 [DE] Fed. Rep. of Germany ....... 3734759

[51] Int. Cl.[5] .......................... C07F 9/58; A01N 43/40
[52] U.S. Cl. ......................................... 514/89; 546/25
[58] Field of Search ............................. 546/25; 514/89

[56] References Cited

U.S. PATENT DOCUMENTS 3,244,586  4/1966  Rigterink ............... 546/25
3,927,004  12/1975  Pawloski ............... 546/25
3,957,801  5/1976  Drabek et al. ......... 546/25

FOREIGN PATENT DOCUMENTS 2350886  5/1974  Fed. Rep. of Germany ........ 546/25

Primary Examiner—Alan L. Rotman
Attorney, Agent, or Firm—Curtis, Morris & Safford

[57] ABSTRACT

Pyridylphosphates, a process for their preparation, agents containing them, and their use as pesticides compounds of the formula I

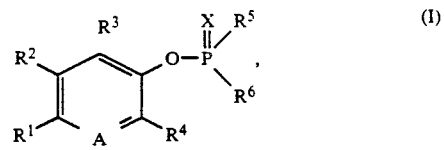

where
A is N or N—>O,
$R^1$, $R^2$ independently of one another are halogen,
X=O or S,
$R^3$ and $R^4$ independently of one another are H, halogen, phenyl, phenylthio, phenoxy, phenylsulfenyl, phenylsulfinyl, phenylsulfonyl, phenylsulfonylamino, phenylamino, phenylcarbonylamino, all of which can be substituted in the phenyl moiety by halogen, alkyl, alkoxy, alkylcarbonyl, alkoxycarbonyl, haloalkoxy, haloalkyl, nitro, dialkylamino, alkylthio, cyano or carboxyl, or are alkyl, alkoxy, alkylthio, alkylcarbonyl, alkoxycarbonyl, haloalkoxy, haloalkyl, alkylsulfenyl, alkylsulfinyl, alkylsulfonyl, cyano, nitro, carboxyl, sulfo, heteroaryl, heteroaryloxy, alkenyl, alkinyl, both of which can optionally be mono- substituted or polysubstituted by halogen, or are amino, monoalkylamino, dialkylamino, it being possible for the two alkyl groups, together with the N atom, to form a 5- to 7-membered ring, or are alkylsulfonylamino, thiocyanato or cyanato and
$R^5$ and $R^6$ independently of one another are alkyl, alkoxy, monoalkylamino, dialkylamino, it being possible for the two alkyl groups together with the N atom to form a 5- to 7-membered ring, or are phenyl, phenoxy, phenylthio, all of which can be substituted by halogen, alkyl, alkoxy, alkylcarbonyl, alkoxycarbonyl, haloalkoxy, haloalkyl, nitro, dialkylamino, alkylthio, cyano or carboxyl, or denote alkylthio, have advantageous insecticidal, acaricidal or nematocidal properties.

6 Claims, No Drawings

PYRIDYL PHOSPHATES, COMPOSITIONS CONTAINING THEM AND THEIR USE AS PESTICIDES

DESCRIPTION

Pyridyl phosphates, a process for their preparation, agents containing them, and their use as pesticides.

The use of (thio)phosphoric and (thio)phosphonic acid derivatives as pesticides is known and has been described in the literature, thus, for example, in U.S. Pat. No. 3,927,004, U.S. Pat. No. 3,244,586 or German Offenlegungsschrift 2,350,886.

New pyridyl phosphates showing advantageous activities against plant pests have been found.

The present invention thus relates to compounds of the formula I

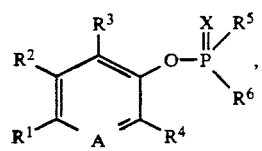

(I)

where
A is N or N→O,
$R^1$ and $R^2$ independently of one another are halogen,
X=O or S,
$R^3$ and $R^4$ independently of one another are H, halogen, phenyl, phenylthio, phenoxy, phenylsulfenyl, phenylsulfinyl, phenylsulfonyl, phenylsulfonylamino, phenylamino, phenylcarbonylamino, all of which can be substituted in the phenyl moiety by halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-haloalkoxy, $(C_1-C_4)$-haloalkyl, nitro, $(C_1-C_4)$-dialkylamino, $(C_1-C_4)$-alkylthio, cyano or carboxyl, or $(C_1-C_6)$-alkyl, $(C_1-C_6)$-alkoxy, $(C_1-C_6)$-alkylthio, $(C_1-C_6)$-alkylcarbonyl, $(C_1-C_6)$-alkoxycarbonyl, $(C_1-C_6)$-haloalkoxy, $(C_1-C_6)$-haloalkyl, $(C_1-C_6)$-alkylsulfenyl, $(C_1-C_6)$-alkylsulfinyl, $(C_1-C_6)$-alkylsulfonyl, cyano, nitro, carboxyl, sulfo, heteroaryl, heteroaryloxy, $(C_2-C_6)$-alkenyl, $(C_2-C_6)$-alkynyl, of which can optionally be monosubstituted or polysubstituted by halogen, or are amino, $(C_1-C_6)$-monoalkylamino, $(C_1-C_6)$-dialkylamino, it being possible for the two alkyl groups, together with the N atom, to form a 5- to 7-membered ring, or are $(C_1-C_6)$-alkylsulfonylamino, thiocyanato or cyanato and $R^5$ and $R^6$ independently of one another are $(C_1-C_6)$-alkyl, $(C_1-C_6)$-alkoxy, $(C_1-C_6)$-monoalkylamino, $(C_1-C_6)$-dialkylamino, it being possible for the two alkyl groups, together with the N atom, to form a 5- to 7-membered ring, or are phenyl, phenoxy, phenylthio, all of which can be substituted by halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-haloalkoxy, $(C_1-C_4)$-haloalkyl, nitro, $(C_1-C_4)$-dialkylamino, $(C_1-C_4)$-alkylthio, cyano or carboxyl, or denote $(C_1-C_6)$-alkylthio.

In this context, heteroaryl denotes pyridyl, pyrrolidyl, furyl or thienyl, or the corresponding oxygen-containing radicals in the case of heteroaryloxy, and alkyl in each case denotes straight-chain or branched alkyl.

Halogen preferably denotes Cl, Br and I.

Preferred compounds of the formula I are those in which X is O or S, A is N, $R^1$ and $R^2$ independently of one another are halogen, $R^3$ and $R^4$ independently of one another are H, halogen, $(C_1-C_6)$-alkyl, $(C_1-C_6)$-alkoxy, $(C_1-C_6)$-alkylthio, $(C_1-C_6)$-monoalkylamino, $(C_1-C_6)$-dialkylamino, phenyl, phenoxy or phenylthio and $R^5$ and $R^6$ independently of one another denote $(C_1-C_6)$-alkyl, $(C_1-C_6)$-alkoxy, $(C_1-C_6)$-monoalkylamino, $(C_1-C_6)$-dialkylamino, phenyl, phenoxy, phenylthio or $(C_1-C_6)$-alkylthio.

Particularly preferred compounds of the formula I are those in which $R^1$ is Cl, Br or I, $R^2$ is Cl or Br, A is N, X is O or S, $R^3$ and $R^4$ independently of one another are H, halogen, $(C_1-C_6)$-alkyl, $(C_1-C_6)$-alkoxy or $(C_1-C_6)$-alkylthio, and $R^5$ and $R^6$ independently of one another denote $(C_1-C_6)$-alkyl, $(C_1-C_6)$-alkoxy, $(C_1-C_6)$-alkylthio, $(C_1-C_6)$-monoalkylamino or $(C_1-C_6)$-dialkylamino.

The present invention also relates to a process for the preparation of the compounds of the formula I, which comprises reacting a compound of the formula II

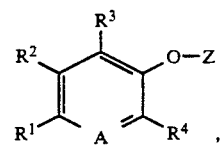

(II)

where Z denotes H, alkali metal or ammonium which can optionally be substituted and $R^1$ to $R^4$ and A have the meanings as given in formula I, with a compound of the formula III

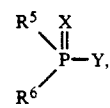

(III)

where Y is halogen and $R^5$, $R^6$ and X have the meanings as given in formula I, the process being carried out in the presence of an acid-binding agent in the case where Z=H.

As a rule, the reactants are employed in approximately stoichiometric amounts; however, an excess of 5-10% of the compound of the formula III can be advantageous.

The process is expediently carried out in the presence of a solvent which is inert towards the reactants. Lower aliphatic ketones, such as acetone or methyl ethyl ketone, alkanols, such as methanol, ethanol or isopropanol, esters, such as ethyl acetate, nitriles, such as acetonitrile, N-alkylated acid amides, such as dimethylformamide, ethers, such as dioxan, glycol dimethyl ether or tetrahydrofuran, chlorinated hydrocarbons, Such as chloroform or carbon tetrachloride, and water, and also mixtures of such solvents, are preferably suitable.

In the event that Z is hydrogen, acid-binding agents are added to the reaction mixture. Acid-binding agents which are preferably employed are the hydroxides and carbonates of alkali metals; however, it is also possible to use tertiary nitrogen bases, such as pyridine or triethylamine.

Where Z is an alkali metal, it preferably denotes Na+ or K+.

The reaction temperatures can be varied within the range 0° to 150° C.; preferably, the reaction is carried out at between +50° C. and +120° C.

The hydroxypyridines of the formula II (Z=H) can be prepared by methods known from the literature (German Offenlegungsschrift 3,545,570). Starting with these hydroxypyridines, the compounds of the formula II where Z is alkali metal or ammonium can be obtained by generally known process steps (Beilstein, Handbuch der organ. Chemie [Handbook of Organic Chemistry], H 21, Vol. 21, P. 46). The halophosphorus compounds of the formula III are known and are readily accessible by customary methods (Houben-Weyl, Methoden der organischen Chemie [Methods of Organic Chemistry], Vol. E2).

The active substances are well tolerated by plants and are suitable for controlling animal pests, in particular insects, arachnids and nematodes which occur in agriculture, in forests, in stored goods and materials, and in the hygiene field. They are active against normally sensitive and resistant species and against all or individual stages of development. The above mentioned pests include:

From the order of the Isopoda, for example *Oniscus asellus, Armadillidium vulgare, Porcellio scaber.*

From the order of the Diplopoda, for example *Blaniulus guttulatus.*

From the order of the Chilopoda, for example *Geophilus carpophagus, Scutigera spec.*

From the order of the Symphyla, for example *Scutigerella immaculata.*

From the order of the Thysanura, for example *Lepisma saccharina.*

From the order of the Collembola, for example *Onychturus armatus.*

From the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis, Schistocerca gregaria.*

From the order of the Dermaptera, for example *Forficula auricularia.*

From the order of the Isoptera, for example Reticulitermes spp.

From the order of the Anoplura, for example *Phylloxeravastatrix, Pemphigus* spp., *Pediculus humanus corporis,* Haematopinus spp., Linognathus spp.

From the order of the Mallophaga, for example Trichodectes spp., Damalinea spp.

From the order of the Thysanoptera, for example *Hercinothrips femoralis, Thrips tabaci.*

From the order of the Heteroptera, for example Eurygaster spp., *Dysdercus intermedius, Piesma quadrata, Cimes lectularius, Rhodnius prolixus,* Triatoma spp.

From the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Naphotettix cincticeps, Lecanium corni, Saissetia oleae, Laodelphax striatellus, Nilaparvata lugens, Aonidiella aurantii, Aspidiotus hederae, Pseudococcus* spp., Psylla spp.

From the order of the Lepidoptera, for example *Pectinophora gossypiella, Bupalus piniarius, Cheimatobia brumata, Lithocolletis blancardella, Ryponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia koehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana.*

From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera, for example Diprion spp., Hoplocampa spp., Lasius spp., *Monomorium pharaonis,* Vespa spp.

From the order of the Diptera, for example Aedes spp., Anopheles spp., Culex spp., *Drosophila melanogaster,* Musca spp , Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit, l Phorbia* spp., *Pegomyia hyoscyami, Ceratitis capitato, Dacus oleae, Tipular paludosa.*

From the order of the Siphonaptera, for example *Xenopsylla cheopis,* Ceratophyllus spp., From the order of the Arachnida, for example *Scorpio maurus, Latrodectus mactans.*

From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp..

Furthermore, the compounds have an excellent activity against nematodes which damage plants, for example those of the genera Meloidogyne, Heterodera, Ditylenchus, Aphelenchoides, Radopholus, Globodera, Pratylenchus, Longidorus and Xiphinema.

The invention also relates to agents containing the compounds of the formula I in addition to suitable formulation auxiliaries.

The agents according to the invention generally contain 1 to 95% by weight of the active substances of the formula I.

They can be formulated in various ways, as determined by the biological and/or chemical/physical parameters. Thus, suitable formulation possibilities are: wettable powders (WP), emulsifiable concentrates (EC), aqueous solutions (SC), emulsions, sprayable solutions, oil-based or water-based dispersions (SC), suspoemulsions (SC), dusting agents (DP), seed-dressing agents, granules in the form of microgranules, granules for spraying, coated granules and granules impregnated by adsorption, water-dispersable granules (WG), ULV formulations, microcapsules, waxes or baits.

These individual formulation types are known in principle and are described, for example, in: Winnacker-Küchler, "Chemische Technologie" [Chemical Technology], Vol. 7, published by C. Hauser, Munich, 4th ed. 1986; van Falkenberg, "Pesticides Formulations", Marcel Dekker N.Y., 2nd ed. 1972-73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd ed., Darland Books, Caldwell N.J.; H.v.Olphen, "Introduction to Clay Colloid Chemistry", 2nd ed., J. Wiley & Sons, N.Y.; Marschen, "Solvents Guide", 2nd ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc. N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Vol. 7, published by C. Hauser, Munich, 4th ed. 1986.

Based on these formulations, it is also possible to prepare combinations with other pesticidally-active substances, fertilizers and/or growth regulators, for example in the form of a ready mix or as a tank mix.

Wettable powders are preparations which are uniformly dispersible in water and which, besides the active substance and in addition to a diluent or inert substance, also contain wetting agents, for example polyoxyethylated alkylphenols, polyoxyethylated fatty alcohols, alkylsulfonates or alkylphenolsulfonates, and dispersing agents, for example, sodium ligninsulfonate, sodium 2,2'-dinaphthylmethane-6,6'-disulfonate, sodium dibutylnaphthalinesulfonate, and also sodium oleylmethyltaurate. Emulsifiable concentrates are prepared by dissolving the active substance in an organic solvent, for example butanol, cyclohexanone, dimethylformamide, xylene and also higher-boiling aromatic substances or hydrocarbons, with the addition of one or more emulsifiers. Emulsifiers which can be used are, for example, calcium salts of alkylarylsulfonic acids, such as calcium dodecylbenzenesulfonate, or non-ionic emulsifiers, such as fatty acid polyglycol esters, alkylaryl polyglycol ethers, fatty alcohol polyglycol ethers, condensation products of propylene oxide and ethylene oxide, alkyl polyethers, sorbitan fatty acid esters, polyoxyethylene sorbitan fatty acid esters or polyoxyethylene sorbitol esters.

Dusting agents are obtained by grinding the active substance with finely dispersed solid substances, for example talc, natural clays, such as kaolin, bentonite, poryphillite or diatomaceous earth. Granules can be prepared either by spraying the active substance on to adsorptive inert material in the form of granules or by applying concentrates of active substance by means of adhesives, for example polyvinyl alcohol, sodium polyacrylate or, alternatively, mineral oils, on to the surface of carrier substances such as sand, kaolinites or of inert material in the form of granules. It is also possible to prepare granules of suitable active substances in the manner customary for the production of fertilizer granules, if desired, in a mixture with fertilizers.

The concentration of active substance in wettable powders is, for example, about 10 to 90% by weight, the difference to 100% by weight is composed of the customary formulation constituents. In the case of emulsifiable concentrates, the concentration of active substance is about 5 to 80% by weight. Formulations in the form of dust usually contain 5 to 20% by weight of active substance, sprayable solutions about 2 to 20% by weight. In the case of granules, the amount of active substance partly depends on the active compound being present in the form of a liquid or a solid and which granulating auxiliaries, fillers, etc. are used.

In addition, the mentioned formulations of active compound contain, if appropriate, the adhesives, surfactants, dispersing agents, emulsifiers, penetrating agents, solvents, fillers or carriers which customary in each case.

If appropriate, the concentrates which are present in the commercially available form are diluted in the customary manner for application, for example with water in the case of wettable powders, emulsifiable concentrates, dispersions and occasionally microgranules. Preparations in the form of dust and in the form of granules and also sprayable solutions are usually not diluted with further inert substances prior to application.

The application rate required varies with the external conditions, such as temperature, humidity and the like. It can vary within relatively wide limits, for example between 0.005 and 10.0 kg/ha or more of active substance, preferably, however, it is between 0.01 and 5 kg/ha.

The active substances according to the invention, in particular those of the examples listed, can be present in the commercially available formulations and in the use forms prepared from these formulations in a mixture with other active substances, such as insecticides, attractants, sterilants, acaricides, nematicides, fungicides, growth regulating substances or herbicides. The insecticides include, for example, phosphoric acid esters, carbamates, carboxylic acid esters, formamidines, tin compounds, substances produced by microorganisms and the like. Preferred components for mixtures are:

1. From the group of the phosphoric acid esters azinphos-ethyl, azinphos-methyl, 1-(4-chlorophenyl)-4-(O-ethyl, S-propyl)phosphoryloxypyrazole (TIA-230), chlorpyrifos, coumaphos, demeton, demeton-S-methyl, diazinon, dichlorvos, dimethoate, ethoprophos, etrimfos, fenitronthion, fenthion, heptenophos, parathion, parathion-methyl, phosalone, pirimiphos-ethyl, pirimiphos-methyl, profenofos, prothiofos, sulprofos, triazophos, trichlorphon.

2. From the group of the carbamates aldicarb, bendiocarb, BPMC (2-(1-methylpropyl)phenylmethyl carbamate), butocarboxim, butoxicarboxim, carbaryl, carbofuran, carbosulfan, cloethocarb, isoprocarb, methomyl, oxamyl, primicarb, promecarb, propoxur, thiodicarb.

3. From the group of the carboxylic acid esters allethrin, alphamethrin, bioallethrin, bioresmethrin, cycloprothrin, cyfluthrin, cyhalothrin, cypermethrin, deltamethrin, alpha-cyano-3-phenyl-2-methylbenzyl 2,2-dimethyl-3-(2-chloro-2-trifluoromethylvinyl)cyclopropancarboxylate (FMC 54800), fenpropathrin, fenfluthrin, fenvalerate, flucythrinate, flumethrin, fluvalinate, permethrin, resmethrin and tralomethrin.

4. From the group of the formamidines amitraz, chlordimeform

5. From the group of the tin compounds azocyclotin, cyhexatin and fenbutatin oxide 6. Others abemetin, Bacillus thuringiensis, bensultap, binapacryl, bromopropylate, buprofecin, camphechlor, cartap, chlorobenzilate, chlorfluazuron, 2-(4-chlorophenyl)-4,5-diphenylthiophene (UBI-T 930), chlofentezine, 2-naphthylmethyl cyclopropanecarboxylate (Ro 12-0470), cyromacin, DDT, dicofol, N-(3,5-dichloro-4-(1,1,2,2-tetrafluoroethoxy)phenylaminocarbonyl)-2,6-difluorobenzamide (XRD 473), diflubenzuron, N-(2,3-dihydro-3-methyl-1,3-thiazol-2-ylidene)2,4-xylidine, dinobuton, diocap, endosulfan, fenoxycarb, fenthiocarb, flubenzimine, flufenoxuron, gamma-HCH, hexythiazox, hydramethylnon (AC 217 300) ivermectin, 2-nitrometh-yl-4,5-dihydro-6H-thiazine (SD 52618), 2-nitromethyl-3,4-dihydrothiazole (SD 35651), 2-nitromethylene-1,3-thiazinan-3-yl-carbamaldehyde (WL 108 477), propargite, teflubenzuron, tetradifon, tetrasul, thiocyclam, and triflumaron, nuclear polyhedrosis and granulosis viruses.

The contents of active substance, of the used form prepared from the commercially available formulations, can vary within a wide range. The concentration of active substance, of these forms, can be 0.0001 to 100% by weight of active substance, preferably between 0.001 and 1% by weight. The application is carried out in a customary manner which is chosen to suit the use forms.

The active substances according to the invention are also suitable for controlling ecto- and endoparasites, preferably of insects living as ectoparasites, in the field of veterinary medicine or in the field of animal keeping.

Here, the active substances according to the invention are applied in a known manner, such as by oral application in the form of, for example, tablets, capsules, drinks and granules, or by dermal application in the form of, for example, dipping, spraying, pouring-on, spotting-on and powdering.

The dosages of and formulations suitable in each case depend in particular on the species and the stage of development of the livestock and also on the degree of infestation, and they can be determined and prescribed without difficulty by the customary methods. In cattle, for example, the new compounds can be employed in dosage rates of 0.1 to 100 mg/kg of body weight.

The examples below are intended to illustrate the invention.

A. Formulation examples a) A dusting agent is obtained by mixing 10 parts by weight of active substance and 90 parts by weight of talc as the inert substance and comminuting the mixture in a hammer mill.

b) A wettable powder which is readily dispersible in water is obtained by mixing 25 parts by weight of active substance, 65 parts by weight of kaolin-containing quartz as the inert substance, 10 parts by weight of potassium ligninsulfonate and 1 part by weight of sodium oleoylmethyltaurate as the wetting and dispersing agents, and grinding the mixture in a pinned disk mill.

c) A dispersion concentrate which is readily dispersible in water is prepared by mixing 40 parts by weight of active substance with 7 parts by weight of a sulfosuccinic acid monoester, 2 parts by weight of a sodium ligninsulfonate and 51 parts by weight of water, and grinding the mixture in a ball mill to a fineness of less than 5 microns.

d) An emulsifiable concentrate may be prepared from 15 parts by weight of active substance, 75 parts by weight of cyclohexanone as the solvent and 10 parts by weight of oxethylated nonylphenol (10 EO) as the emulsifier.

e) Granules may be prepared from 2 to 15 parts by weight of active substance and an inert granule support material, such as attapulgite, pumice granules and/or quartz sand. A suspension of the spray powder of Example b) having a solids proportion of 30% is expediently used, and this suspension is sprayed onto the surface of attapulgite granules, and these are dried and mixed intimately. Here, the proportion by weight of the spray powder is about 5% and that of the inert carrier material is about 95% of the ready granules.

B. Preparation Examples 3.0 g (18.2 mM) of 2,3-dichloro-5-hydroxypyridine, 3.0 g (21.8 mM) of potassium carbonate and 3.4 g (18.2 mM) of O,O-diethyl-thiophosphoryl chloride in 30 ml of acetonitrile were stirred for 3 hours at 70° C. The mixture was then poured into 50 ml of water and extracted with methylene chloride, and the organic phases were extracted thoroughly with water. The organic phase was dried over magnesium sulfate. The mixture was concentrated in a water-pump vaccum, and 4.5 g of O,O-diethyl-O-(5-(2,3-dichloropyridyl)) thiophosphate (78% of theory) were isolated.

The compounds of the formula I listed in the table over-leaf were prepared by this process.

TABLE 1

| Example No. | $R^1$ | $R^2$ | $R^3$ | $R^4$ | $R^5$ | $R^6$ | X | $n_D$ or M.P. (°C.) |
|---|---|---|---|---|---|---|---|---|
| 1 | Cl | Cl | H | H | $OC_2H_5$ | $OC_2H_5$ | O | $n_D^{24}$: 1.5005 |
| 2 | Cl | Cl | H | H | $OCH_3$ | $OCH_3$ | S | $n_D^{25}$: 1.5463 |
| 3 | Cl | Cl | H | H | $OC_2H_5$ | $OC_2H_5$ | S | oil |
| 4 | Cl | Cl | H | H | $OC_3H_7$ | $OC_3H_7$ | S | $n_D^{30}$: 1.5203 |
| 5 | Cl | Cl | H | H | $OC_2H_5$ | $NHC_3H_7(i)$ | S | $n_D^{24}$: 1.5398 |
| 6 | Cl | Cl | H | H | $OC_2H_5$ | $CH_3$ | S | $n_D^{30}$: 1.5512 |
| 7 | Cl | Cl | H | H | $OC_2H_5$ | $SC_3H_7(n)$ | S | $n_D^{22}$: 1.5650 |
| 8 | Cl | Cl | H | H | $OC_2H_5$ | $SCH(CH_3)C_2H_5$ | S | $n_D^{25.5}$: 1.5645 |
| 9 | Cl | Cl | H | H | $N(CH_3)_2$ | $N(CH_3)_2$ | S | 45–47 |
| 10 | Cl | Br | H | H | $OC_2H_5$ | $OC_2H_5$ | S | $n_D^{22}$: 1.5421 |
| 11 | Cl | Br | H | H | $OC_2H_5$ | $OC_2H_5$ | O | $n_D^{21}$: 1.5137 |
| 12 | Br | Cl | H | H | $OC_2H_5$ | $OC_2H_5$ | S | $n_D^{22}$: 1.5486 |
| 13 | Br | Cl | H | H | $OC_2H_5$ | $OC_2H_5$ | O | $n_D^{22}$: 1.5202 |
| 14 | J | Cl | H | H | $OC_2H_5$ | $OC_2H_5$ | S | oil |
| 15 | Cl | Cl | H | Cl | $OC_2H_5$ | $OC_2H_5$ | S | $n_D^{24.5}$: 1.5450 |
| 16 | Br | Cl | H | Br | $OC_2H_5$ | $OC_2H_5$ | S | $n_D^{22}$: 1.5758 |
| 17 | Br | Cl | H | Br | $OC_2H_5$ | $OC_2H_5$ | O | $n_D^{22}$: 1.5482 |
| 18 | J | Cl | H | J | $OC_2H_5$ | $OC_2H_5$ | S | $n_D^{24}$: 1.6341 |
| 19 | Br | Cl | Br | Br | $OC_2H_5$ | $OC_2H_5$ | S | $n_D^{25}$: 1.5923 |
| 20 | Br | Cl | Br | Br | $OC_2H_5$ | $OC_2H_5$ | O | $n_D^{25}$: 1.5476 |
| 21 | Br | Cl | Br | Br | $OC_2H_5$ | $SC_3H_7(n)$ | O | oil |

C. Biological Examples

EXAMPLE 1

A 1 ml-portion of the formulation to be tested, emulsified in water, is applied uniformly to the inside of the lid and to the bottom of a Petri dish. When the film has dried, 10 adult common house flies (*Musca domestica*) are introduced into each of the Petri dishes. The dishes are sealed and kept at room temperature, and the mortality of the experimental animals determined after 3 hours. At 250 ppm (based on the contents of active substance), the formulations 1, 2, 3, 4, 5, 6, 7, 10, 11, 12, 13, 15, 16, 17, 19, 20, 21 show a good activity (100% mortality) against the common housefly.

EXAMPLE 2

10 larvae (L4) of the German cockroach (*Blattella germanica*) are in each case introduced into the Petri dish treated as in Example 1, the dish is closed, and the mortality of the experimental animals is determined after 5 days. At 100 ppm (based on the contents of active substance), the formulations 1, 2, 3, 4, 5, 7, 10, 11, 12, 13, 15, 16 and 17, show a good activity (100% mortality) against the German cockroach.

EXAMPLE 3

The inside of the bottom of a Petri dish was covered with one layer of paper filter, and an amount of 3-5 ml of a semi-synthetic feed ration is applied to it. After cooling, the formulations to be tested are sprayed with water in decreasing concentrations on to the surface of the feed and of the filter paper, and, when the spray deposit has dried on, 10 larvae (L3-L4) of the common cotton worm (*Prodenia litura*) are introduced. The Petri dishes are closed with lids and kept for 7 days at room temperature, and the mortality of the experimental animals is then determined At 1000 ppm (based on the contents of active substance), the formulations 1, 2, 3, 5, 6, 7, 10, 11, 12, 13, 15 and 17 showed a good activity against larvae of the common cotton worm.

EXAMPLE 4

Larvae of the Mexican bean beetle (*Epilachna varivestis*, L III) were treated with the preparation of the desired concentration of active substance, in a spraying apparatus. At the same time, leaves of dwarf French bean (*Phaseolus vulgaris*) were dipped into the respective solution of active substance. When the spray deposit had dried on, the larvae of the beetle were placed onto the bean leaves. After 3 days, the percentage destruction of the larvae was determined. At 250 ppm (based on active substance), the formulations 1, 2, 3, 4, 5, 6, 7, 9, 10, 11, 12, 13, 15, 16, 17 and 18 showed good activity against the Mexican bean beetle.

EXAMPLE 5

Larvae of the last larvae stage of the brown plant hopper (*Nilaparvata lugens*) are place in Petri dishes whose bottoms had been covered in a treated, absorbent paper. Before the animals are introduced, each paper filter is moistened with 2 ml of distilled water and then sprayed with decreasing dosages of the experimental preparation, emulsified in water, corresponding to 600 liters of water/ha. After the animals have been placed into the dishes, the latter are sealed immediately and kept for 24 h under laboratory conditions until they are evaluated. The activity (% mortality) is then determined. At a concentration of active substance of 100 ppm, in the spray liquor, the formulations 1, 3, 5, 6, 10, 11, 12, 13, 16, and 17 showed an activity of 100% against brown plant hoppers.

EXAMPLE 6

Bean plants (*Phaseolus v.*) which were heavily infested with greenhouse red spider mites (*Tetranychus urticae*, complete population) were sprayed with the aqueous dilution of an emulsion concentrate which contained 250 ppm of the specific active substance. The mortality of the mites was checked after 7 days. A destruction of 100% was achieved using the compounds of Examples 2, 3, 4, 5, 6, 7, 10, 11, 12, 13, 15, 16 and 17.

EXAMPLE 7

Small apple trees which were heavily infested with fruit tree red spider mites (*Panonychus ulmi*, complete population) were sprayed with the aqueous dilution of an emulsion concentrate which contained 250 ppm of the specific active substance. The mortality of the mites was checked after 7 days. A destruction of 100% was achieved using the compounds of Examples 3, 5, 10, 12 and 13.

EXAMPLE 8

Field beans (*Vicia faba*) which were heavily infested with cow pea aphides (*Aphis craccivora*) were sprayed with aqueous dilutions of spray powder concentrates containing 250 ppm of active substance until the nearly dripping-wet stage. The mortality of the aphides was determined after 3 days. A destruction of 100% could be achieved using the compounds of Examples 1, 2, 3, 4, 5, 6, 7, 9, 10, 11, 12, 13, 15, 16, 17, 18 and 20.

EXAMPLE 9

Bean plants (*Phaseolus vulgaris*) which were heavily infested with citrus mealybug (*Pseudococcus citri*) were sprayed with aqueous suspensions of spray powder concentrates (in each case 250 ppm of active substance in the spray liquor) until the nearly dripping-wet stage was reached. The plants remained in the greenhouse at 20°-25° C. for 7 days and were then checked. 100% Mortality was determined for the compounds of Examples 1, 2, 3, 4, 5, 6, 7, 9, 10, 11, 12, 13, 15, 16, 17 and 20.

EXAMPLE 10

A formulation in the form of dust was mixed with soil infested with *Meloidogyne incognita*. The soild was then filled into pots and planted with tomatoes. The pots remained in the greenhouse for 4 weeks, and scores of the following scheme were determined:

TABLE 2

| Galls/plant | Score |
|---|---|
| 0 | 1 |
| 1–2 | 2 |
| 3–5 | 3 |
| 6–10 | 4 |
| . | . |
| . | . |
| . | . |
| more than 150 | 9 |

A score of 1 was achieved when the compounds of Examples 3, 5, 10, and 12 were employed at a concentration of 15 ppm.

EXAMPLE 11

Larvae of the giant death's head cockroach (*Blaberus craniifer*, L 4) were treated topically with active substance dissolved in methanol. After 7 days, the percentage destruction of the larvae was determined. At application rates of $2 \times 10^{-4}$ g of a.i., the formulations 3, 5, 10 and 13 showed a good activity (100% mortality).

EXAMPLE 12

Larvae of the tobacco hornworm (*Manduca sexta*, L 4) were treated topically with active substance dissolved in acetone. After 7 days, the percentage destruction of the larvae was determined. At application rates of $2 \times 10^{-4}$ g of a.i., the formulations 3, 5, 10 and 13 showed a good activity (100% morality).

We claim:

1. The compound which is O,O-dimethyl-O-(5-(2,3-dichloropyridyl))thiophosphate.

2. An insecticidal composition for controlling noxious insects comprising an insecticidally effective amount of a compound of formula I as claimed in claim 1 and an insecticidally suitable carrier therefor.

3. A method for controlling noxious insects which comprises applying an insecticidally effective amount of a compound of formula I as claimed in claim 1 to an insect or to a plant, surface or substrate infested with said insect.

4. An insecticidal composition as claimed in claim 2, wherein said insect is an acarid or a nemotode.

5. A method as claimed in claim 3, wherein said insect is an acarid or a nematode.

6. The compound which is O,O-diethyl-O-(5-(2,3-dichloropyridyl))thiophosphate.

* * * * *

UNITED STATES PATENT AND TRADEMARK OFFICE
CERTIFICATE OF CORRECTION

PATENT NO. : 5,075,294

DATED : December 24, 1991

INVENTOR(S) : Koch et al.

It is certified that error appears in the above-identified patent and that said Letters Patent is hereby corrected as shown below:

Column 12, line 5, after "compound" delete "of formula I"; and line 9, after "compound" delete "of formula I".

Signed and Sealed this

Twenty-sixth Day of January, 1993

Attest:

STEPHEN G. KUNIN

*Attesting Officer*      *Acting Commissioner of Patents and Trademarks*